United States Patent [19]

Nappholz et al.

[11] Patent Number: 5,713,937
[45] Date of Patent: Feb. 3, 1998

[54] PACEMAKER PROGRAMMER MENU WITH SELECTABLE REAL OR SIMULATED IMPLANT DATA GRAPHICS

[75] Inventors: Tibor A. Nappholz, Englewood; Bruce Steinhaus, Parker; Chih-ming James Chiang, Highlands Ranch, all of Colo.; Alan D. Bernstein, Montvale, N.J.

[73] Assignee: Pacesetter, Inc., Sylmar, Calif.

[21] Appl. No.: 554,483

[22] Filed: Nov. 7, 1995

[51] Int. Cl.⁶ .............................. A61N 1/365; A61N 1/37; A61N 1/362
[52] U.S. Cl. .................................... 607/30; 607/27
[58] Field of Search .................... 607/27, 30, 32, 607/59, 60

[56] References Cited

U.S. PATENT DOCUMENTS

| | | | |
|---|---|---|---|
| 4,791,936 | 12/1988 | Snell et al. | 607/27 |
| 4,809,697 | 3/1989 | Causey, III et al. | 607/30 |
| 4,979,506 | 12/1990 | Silvian et al. | 607/31 |
| 5,372,607 | 12/1994 | Stone et al. | 607/30 |
| 5,421,830 | 6/1995 | Epstein et al. | 607/30 |
| 5,431,691 | 7/1995 | Snell et al. | 607/27 |

*Primary Examiner*—Marvin M. Lateef
*Assistant Examiner*—Carl H. Layno
*Attorney, Agent, or Firm*—Gottlieb, Rackman & Reisman

[57] ABSTRACT

A graphic user interface for a cardiac implant, such as an implant programmer, includes image generators for generating multiple images on a screen, each image corresponding to as representation of a parameter related to the operation of the implant or a cardiac function, and an indicia generator for superimposing on the images an indicia indicative of the interrelation between the parameters. The indicia allows a user to obtain a clear understanding and appreciation of the cause and effect rules between various cardiac parameters and/or functions, the parameters or functions could be actual, i.e., obtained from the implant and/or the patient's heart, or they can be simulated to provide the user an indication on how the pacemaker will operate under these simulated conditions parameters.

20 Claims, 6 Drawing Sheets

PACEMAKER PROGRAMMER MENU WITH SELECTABLE REAL OR SIMULATED IMPLANT DATA GRAPHICS

BACKGROUND OF THE INVENTION

1. Field of Invention

This invention pertains to programmers used to initialize, monitor and modify the operation of implanted pacemakers or similar heart stimulation devices, and more particularly to a programmer having an improved graphic interface selected to provide a wide range of information to the physician.

2. Description of the Prior Art

Programmers are used to initialize and service various implanted devices for cardiac therapy. These devices include pacemakers, cardioversion/defibrillator devices, and so on. Presently, typical programmers provided to the physician are generally the size and shape of a portable or laptop computer. Communication with an implanted device is accomplished through inductive coupling by using an accessory connected to the programmer, commonly called a "wand." The programmers further include a screen for displaying alphanumeric information, and, optionally, to display graphic information such, as for example, an ECG. The programmer may also include a printer for printing of various information, such as the programming parameters set for a particular pacemaker, data logged by the pacemaker for a preselected period, or an ECG.

A disadvantage of the present programmers involves the techniques used to both collect and display information to the physician. The ECG is the only graphic information presented and it is essentially nothing more than a time-dependent graph of the QRST complex sensed in the heart. The remaining information is presented to the physician in the form of lists of parameters and associated parameter values.

Similar table formats are used to provide other information as well. To change the programming, or initiate the programming for a newly implanted pacemaker, the physician must go through several pages of other tables and, in response to prompts, must select the various operational parameters. This whole process is time consuming and requires a steep and long learning curve for the physician. Moreover, because information is displayed by, or fed to the programmer in form of these tables, the physician lacks an intuitive feeling for these parameters and can interpret the same only after years of experience. Moreover, this problem is intensified as the complexity of implantable devices, and concurrently, the number of parameters increases.

OBJECTIVE AND SUMMARY OF THE INVENTION

In view of the above-mentioned disadvantages of the prior art, it is an objective of the present invention to provide a programmer having a user interface which presents information in a clear, succinct manner such that a physician can at one glance, establish the status and the configuration of a device, with clear indications of its operational limits.

A further objective is to provide a programmer that is flexible so that it can be used for a wide variety of implantable devices, such as pacemakers for both brady- and tachy-cardia, cardioversion/defibrillation devices, and so on.

A further objective of the invention is to provide a programmer having a user friendly graphic interface which can be readily used without the need for consulting bulky manuals, and/or spending long hours in training.

Another objective is to provide a programmer with means of displaying graphically a simulation of the heart and a cardiac therapy device as well as their present operation and simulated operation when the device's operational parameters are changed.

A further objective is to provide a programmer which can reprogram or reconfigure the implanted device by manipulating the graphic symbols and presentations in such a manner that the graphic presentation will display the new programmed parameters to scale in intervals and amplitudes.

A further objective is to supply a help function for a pacemaker programmer such that pointing at any object or a sequence will present to the user information about a corresponding event or parameter.

Other objectives and advantages of the invention shall become apparent from the following description of the invention.

Briefly, a programmer constructed in accordance with this invention includes a user interface consisting of a display and means for displaying on said display several graphic elements, including an element showing a time dependent parameter related to a cardiac function, such as an ECG, and another element showing a relationship between two cardiac function parameters. Importantly, the user interface further includes means for generating indicia on said display relating events from one graphic elements to events on the other graphic element.

The programmer further includes simulating means for simulating the response of a patient's heart to certain functional parameters, and selection means for selectively displaying on said display graphic elements descriptive of either actual cardiac functions or simulated cardiac functions as determined by said simulating means.

The simulator further has the facility of responding to the movement of icons by the user into an overlapping relationship with the timing sequences. These icons can represent either stimuli or natural heart beats such as "P----" "R----" waves.

DETAILED DESCRIPTION OF THE INVENTION

Figure 1:
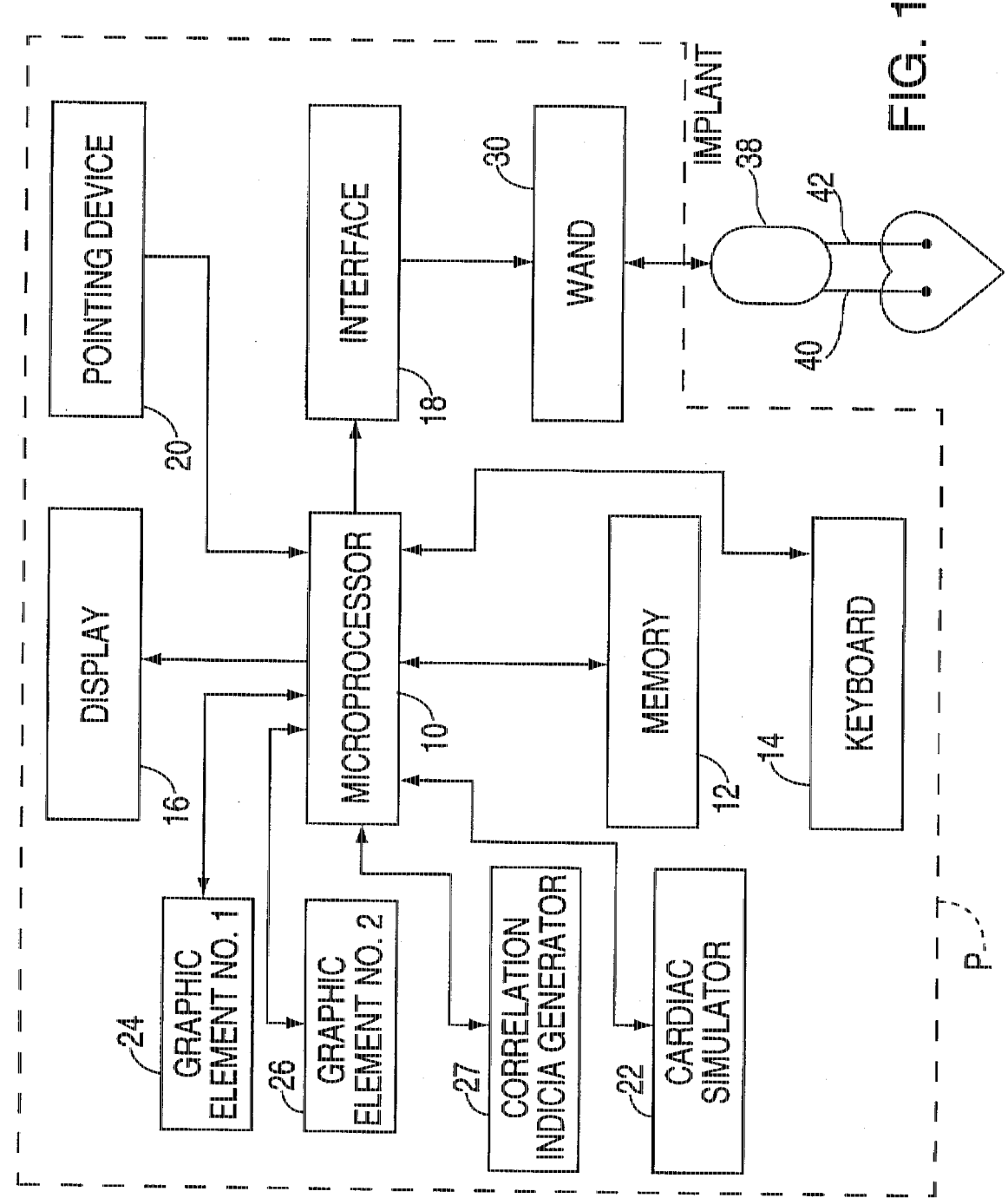
FIG. 1 shows a block diagram of a programmer constructed in accordance with this invention.

Referring now to FIG. 1, a programmer P constructed in accordance with this invention includes a microprocessor 10, a memory 12, a keyboard 14, and a display 16. An interface 18 provides communication through a wand 30 with an implant 38. The implant 38 is coupled to a patient's heart 36 by leads 40, 42. The memory 12 holds programming information for using the programmer 10 to establish communication with the implant 38, collect information from the implant 38, and generate operational parameters (and programming steps, if necessary) and send the same to the implant 38. Additional information or selections by a physician are entered on keyboard 14 and/or a pointing device, commonly referred to as a 'mouse', 20, or another similar pointing device which can be used to select information from the display.

In accordance with this invention, the programmer also includes a cardiac simulator 22, graphic element generators 24, 26 and a correlation indicia generator 27. The programmer P contains other graphic element generators for generating graphic elements on display 16, as discussed below but which have been omitted for the sake of simplicity. The graphic element generators 24, 26, the cardiac simulator 22, keyboard 14, display 16, keyboard 14, pointing device 20, all cooperate with the microprocessor 10 to form an easy to use user interface.

Figure 2:
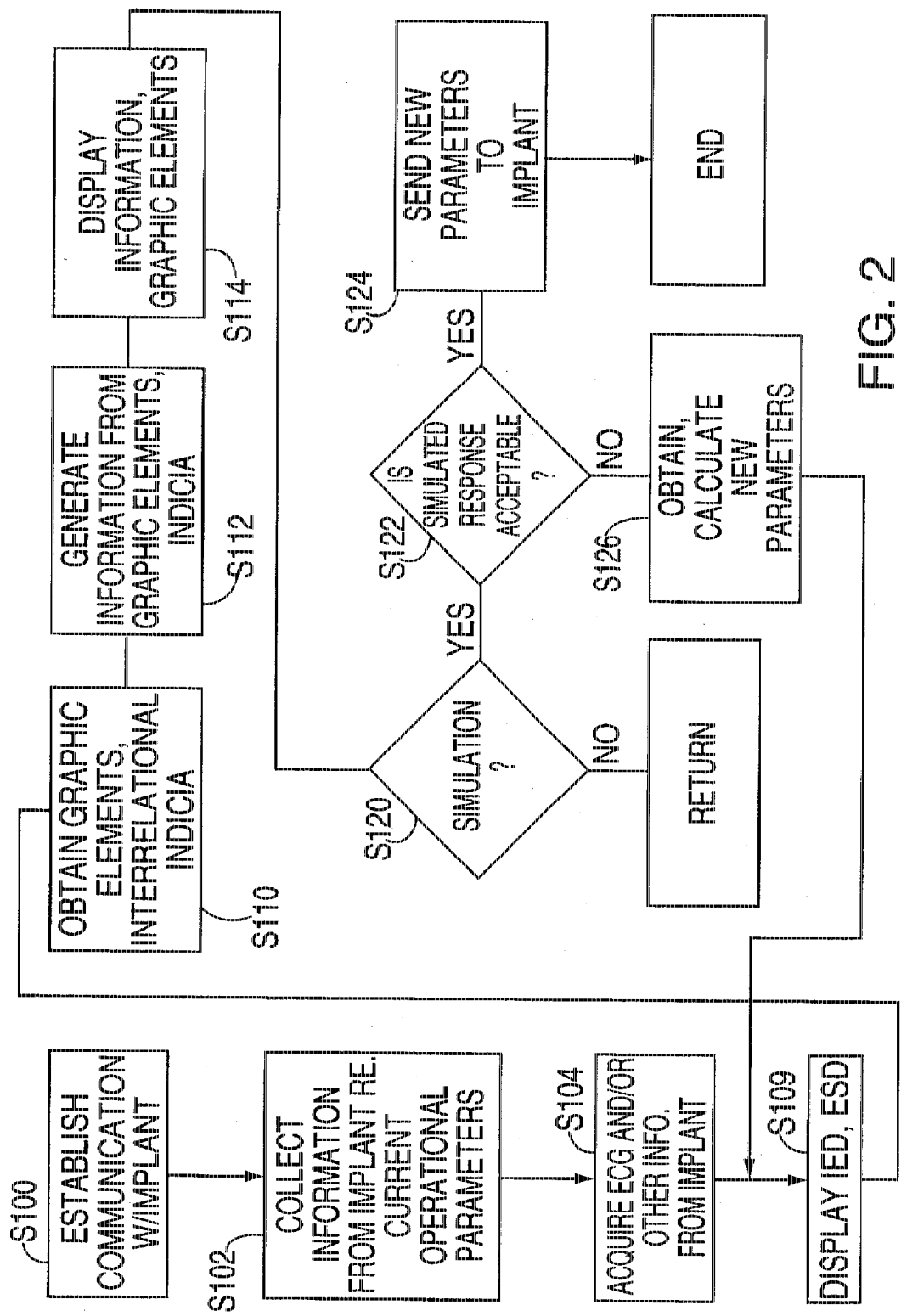
FIG. 2 shows a block diagram descriptive of the operation of the programmer.

The operation of the programmer P is best described in conjunction with the flow chart of FIG. 2. As previously mentioned, in order to initialize or service an implanted device 38, the programmer P first establishes communication with the device through interface 18 and wand 30. This process is indicated in FIG. 2 by step 100. Once communication has been established (i.e., a handshaking protocol takes place), the microprocessor 10 retrieves various information from the implant 38. This information may be patient and/or device specific, i.e., it may describe the implantation date, the name and physical condition of the patient, as well as the serial and model number of the implant 38. Importantly, the current operational parameters of the implant 38 are also downloaded into programmer P. For initialization, these parameters may be set at default values. Finally, various information logged over a preselected time period, such as a current ECG, and a threshold impedance may also be stored by the implant 38 and downloaded to the programmer 10, as indicated by step S104.

Figure 3:
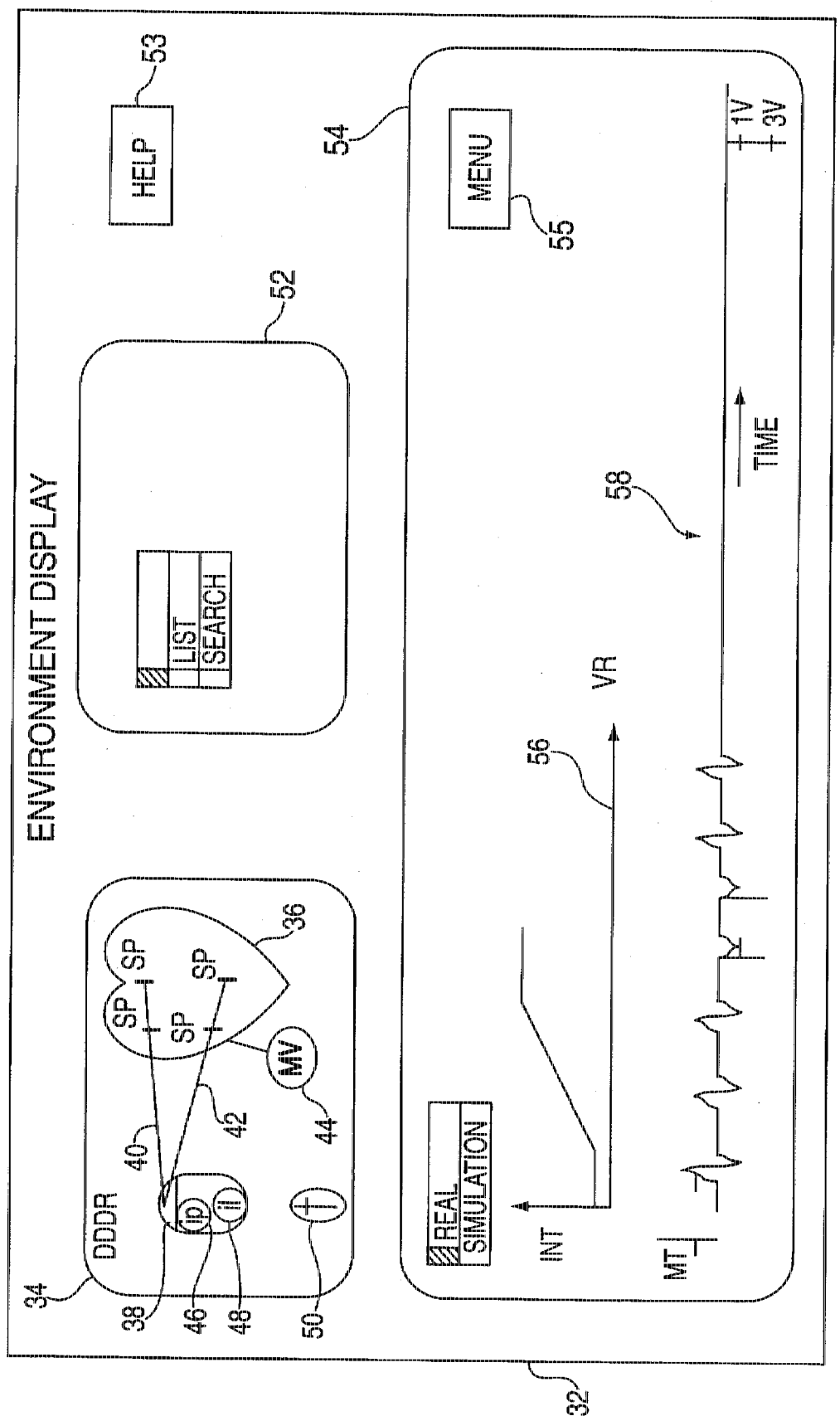
FIG. 3 shows a main screen of the display.

After interrogation by the programmer P, several graphic elements are displayed on screen 32 as shown in FIG. 2, step S109 and FIG. 3. The screen 32 is partitioned into several sections. One section 34 is designated the Implant Environment Display (IED) for showing the implant and its connections of the heart of the patient. Another section 52 is designated the data base section and is used to access, and if necessary, modify data stored in the programmer P. A third section 54 is designated the Event Sequence Display (ESD). Finally, a section 53 is designated HELP and is provided to assist the user with various functions of the programmer P.

As mentioned before, the IED is dedicated to show the implant and its relationship to the heart. More particularly, on FIG. 3 it is indicated that the implant 38 is coupled to the heart 36 by an atrial lead 40 and a ventricular lead 42. The labels SP in the heart 36 adjacent to the ends of the leads 40, 42 indicate that each lead is being used for both Sensing and Pacing. These can be changed by activating and choosing from the Option Box (OB) discussed below.

The section IED 34 also includes several 'hypertext' type labels as well. These labels include several characters surrounded by circles. One such label 44 disposed near the heart 36 bears the letters MV. Other such labels 46 and 48 with the letters 'ip' and 'il' respectively are associated with the implant 34.

A cursor 50 can be moved across display 32 via the keyboard 14 or pointing device 20. When labels of the IED are selected by the user with the cursor 50 or other means, a corresponding Option box appears showing a list of parameters or other information related to the selected hypertext window. For example, when the label 44 is selected, an Option box (OB) appears on screen 32. This OB lists choices such as: MV—On/Off PIG—On/Off, ESD: On/Off, etc. When the label 46 is selected, an option box for "Implant Parameters" is displayed. The Option Box for "IP" will have choices such as: List Parameters: Yes/No; ESD: A/V/AV/ECG/Off, ESD: Full/Standard. The "List Parameters" is a convenience option allowing all the parameters to be programmed from the graphic displays. The ESD option specifies the graphic information to be presented on the display ESD section 54. When A or V is selected, atrial or ventricular activity is displayed, respectively. The AV choice yields a display showing both atrial and ventricular activity. The choice ECG yields an ECG presentation as shown in FIG. 3 in the ESD 54, at 58. "Full" indicates that all refractory and blanking times are displayed. The "standard" choice does not show the refractory and blanking times.

Similarly choosing the label 'il' yields a display of the logged information. This information may be displayed on the modified ESD which will show events over a time period starting from the time last programming was done. The "DDDR" shown in the upper left hand corner indicates the mode of operation of pacemaker 38.

The data base section 52 includes a list of commands such as 'LIST' and 'SEARCH'. Selecting the 'LIST' command yields a list of information in the data base. This will be information on pulse generators, programming sequences, simulation sequences, etc. Selecting the 'SEARCH' command permits a user searching for a particular programmable parameter, simulation, pulse generator, etc. The selection of commands is also performed by using the pointing cursor 50 described above.

Figure 6:
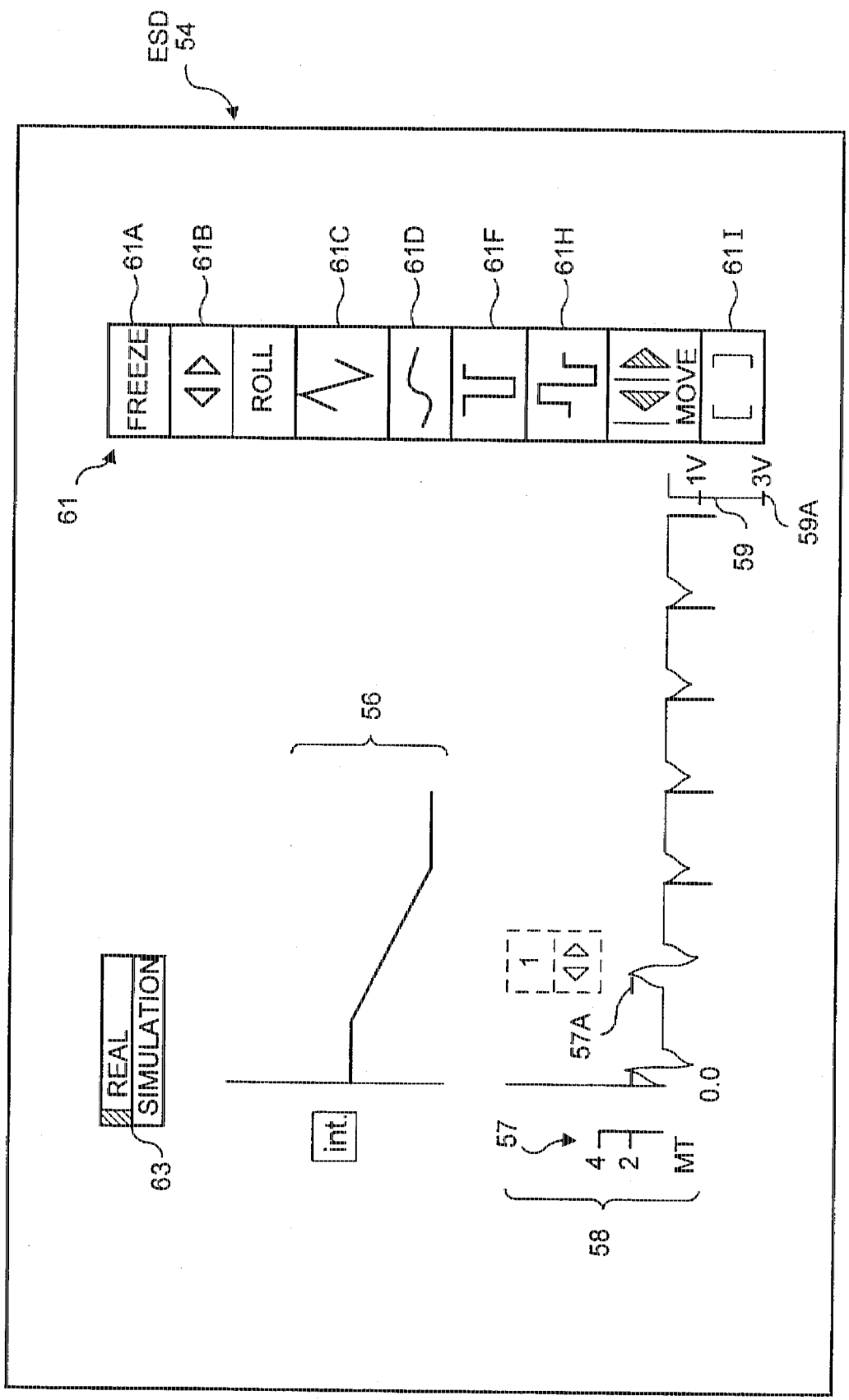
FIG. 6 shows the use of icons for simulation purposes.

Section 54 of the display 32 is the ESD section used to show the graphic information selected with the option boxes for the IP and MV labels discussed above. Details of this section are shown in FIG. 6. Importantly, this section 54 is used to display two different types of graphs. The first type of graph 56 is a parameter inter-relational graph (PIG) i.e., a graph which shows the relationship between two operational parameters of the implant 38. This section is activated by the option box associated with the MV label. For example, the graph 56 may be showing the AV delay as a function of the ventricular pacing rate (VR).

The second graph 58 of ESD 54 shows the event sequence diagram selected with OB 51 associated with the IP label 46. The information for these two graphs 56, 58 is provided by the graphic elements 24 and 26 respectively based on data received from the microprocessor 40. In essence these are individual windows.

Referring now to FIG. 6, the ESD 54 includes the two types of graphs, PIG 56 and ECG 58. In addition, the display includes various other indicia. Once such indicia is the sensing threshold 57 disposed on the right side of display 58. This indicia is used to indicate the current sensing threshold of the patient's heart and is calibrated in millivolts. The threshold level may be repeated as a horizontal bar 57A adjacent to an R-wave. Another indicia is the current ventricular level 59 calibrated in volts.

Also provided on ESD 54 is a menu bar 55. When selected, the menu bar 55 is displayed by a plurality of control icons 61. These icons when selected and dragged over the graph 58, allow the user to vary the characteristics of the graphs 56, 58 or the parameters displayed thereon. For example, the pacing pulse amplitude may be increased or decreased by pointing out a pacing pulse on the ECG, or if there is no pacing pulse, placing one with ICON 61F.

The other indicia on display ESD 54 is the real/simulation indicia 63. This indicia shows whether the graphs 54, 56 are based on real data from pacer of data from simulator.

The EXPAND function selected in FIG. 6 by icon 61B is an important feature for both interrogation and diagnosis. The expanded screen fulfills the need for insight into what is happening in a specific location on the ESD or PIG graphs and also gives insight into the program used parameters.

Figure 5:
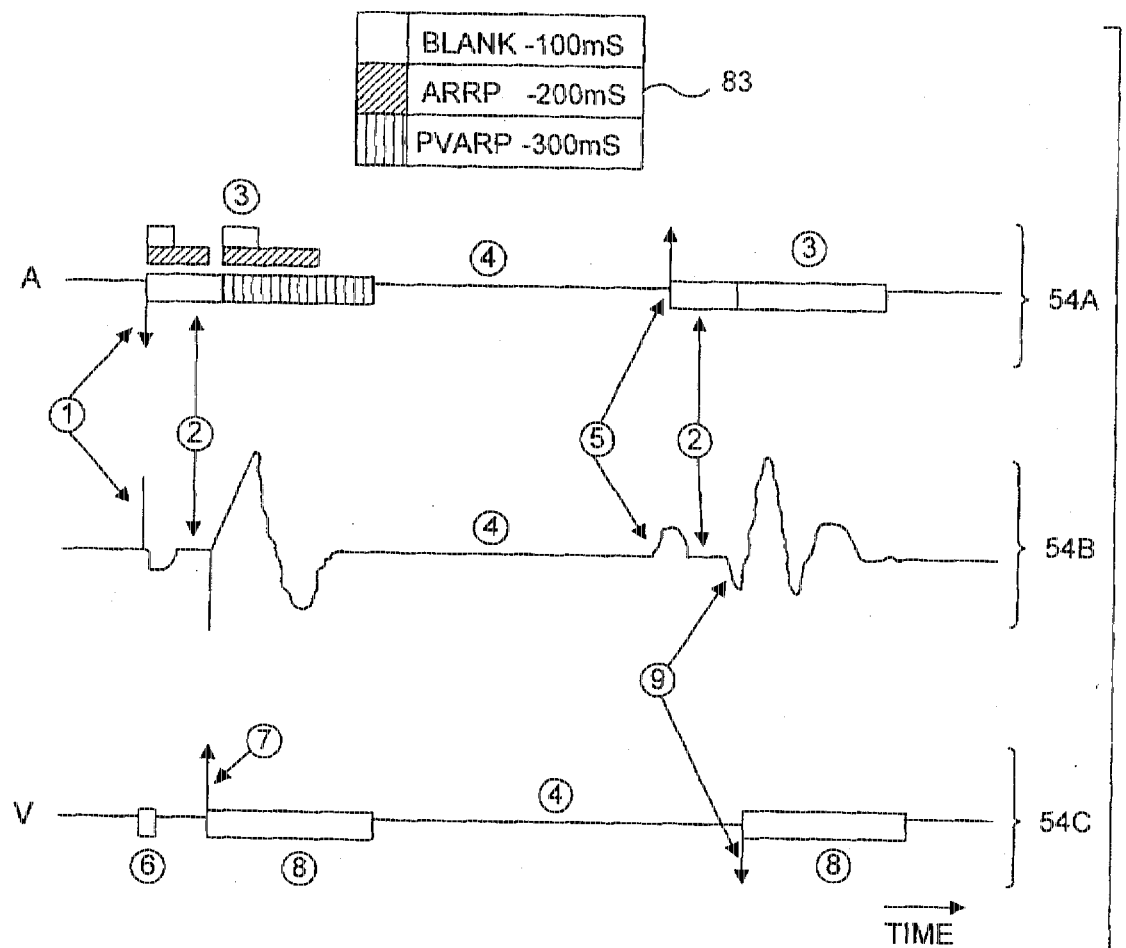
FIG. 5 shows the "help" function which reveals, quantifies and explains various parameters.

As shown in FIG. 5 graph 54 is expanded (in response to selecting the icon) to three time variant charts 54A, 54B, 54C. Chart 54B in this case is a surface ECG. The various artefacts on these charts are defined in the table at the bottom of the Figure. Pointing to a region on any charts presents the various controls parameters that occur in this region and are displayed by numerical displays such as display 83. As an example, pointing to a region such as the "R" wave would show periods 3 and 8, i.e., PVARP (extension if program used and "R" is a PVC), ventricular refractory periods, resetable refractory periods etc. The process is preferably a nested process, meaning that each display could allow access to further detail. The process also reveals an Option Box (OB) (not shown) which displays the actual values of parameters and provide the option of changing the parameters either for the implant or the simulation (shown at 85 in FIG. 5).

If the ESD is in "simulation" mode, then various "Pace" and "Sense" events can be placed into the ESD display and the resultant timing cycles displayed.

While it is very helpful to the user to have these two graphs shown simultaneously, the display alone may still be deficient in that it does not show a cause-and-effect relationship. In other words, merely by looking at these two graphs, the user does not get a sense of how certain points on one graph are related to points on the other graph. Therefore, an important feature of the invention is that the correlating indicia generator 26 generates graphic elements which provide an indicia for correlating the two graphs 56, 58 (this indicia has been omitted from FIGS. 3 and 6 for the sake of clarity.)

Figure 4:
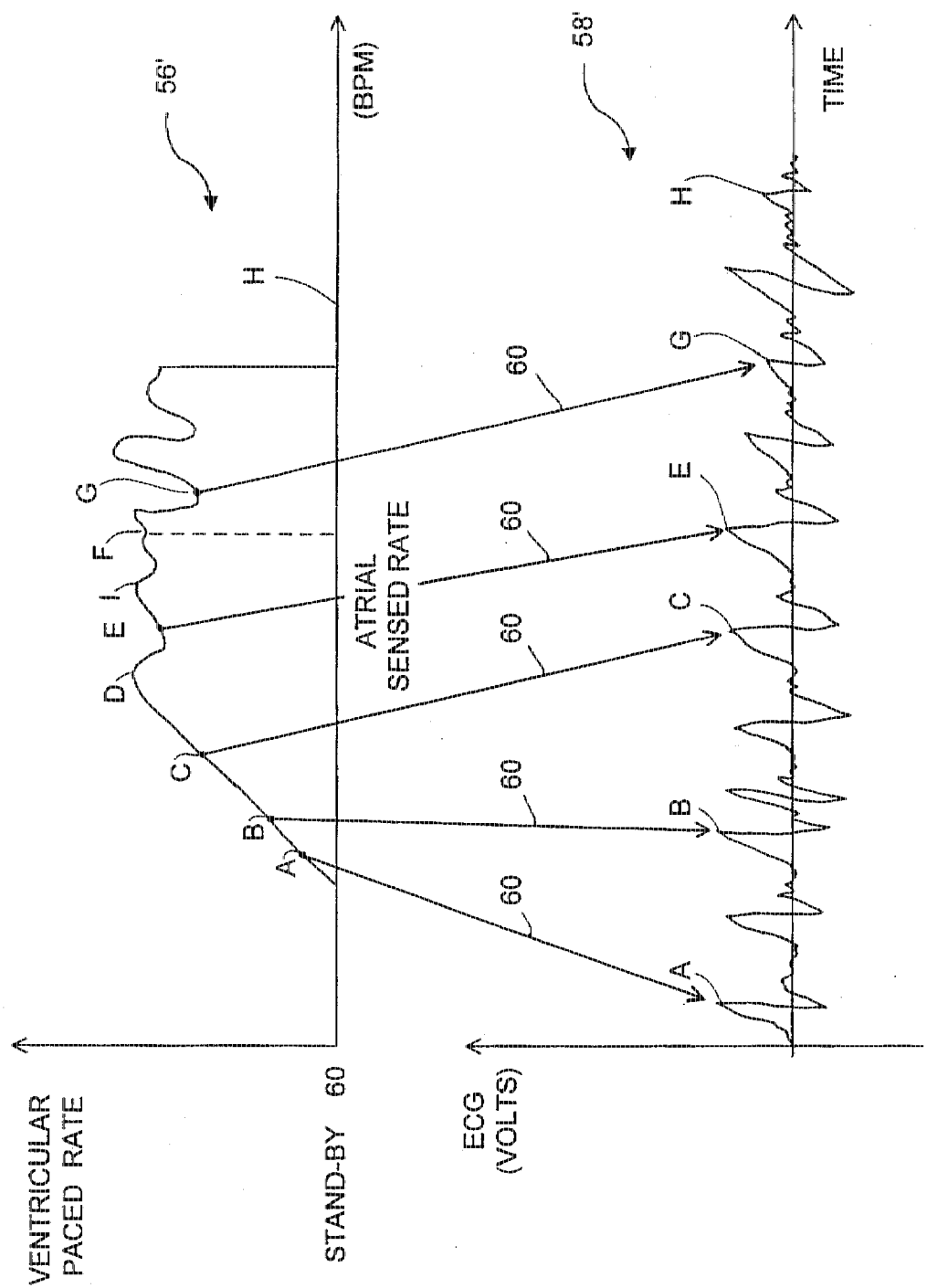
FIG. 4 shows how the two graphic elements and the correlation indicia are shown on the display of FIG. 3.

An example illustrating this correlation indicia feature is shown in FIG. 4. In this Figure, graph 56' shows a classic representation of the ventricular pace rate (VPR) as a function of atrial sensed rate (ASR) as applied by the implant 38 using a Wenckebach technique. The graph 58' shows an ECG for the patient's heart while the pacing defined in graph 56' is applied. In order to show the correlation between these two graphs 56', 58', a plurality of indicia elements are provided. These indicia elements can be in the form of lines such as lines 60 connecting particular points on graph 56' to corresponding points on graph 58'. Alternatively, or in addition, certain points on graph 56' are identified by letters such as A, B, C, ... H. The corresponding points on graph 58' are identified by the same letters. Thus when the QRST complex identified by letter A on graph 58' is sensed by the pacemaker, the pacemaker has been operating in the mode identified by letter A on graph 56'. Of course other types of graphic elements can be used as correlating indicia elements, such as color, (i.e., the corresponding portions of graphs 56', 58' can be represented by the same color), line type, (corresponding portions of graphs 56', 58' could be represented by the same type of line, i.e. thick, thin, dotted, etc.) and so on.

In this manner, the display portion 54 of the Figure with the two graphic elements 56, 58 and the correlation indicia 60 provides comprehensive representation of the operation of the heart 36 and the implant 38.

Another feature of the present invention is that the user has the option of selecting new parameters and determining how the implant will function with these parameters without actually operating the implant with the selected parameters. Prior to this invention, if a physician decided to change the pacemaker parameters, he had to enter these parameters into the pacemaker first, and then request the patient to go through various exercises to charge the hear and monitor the response of the pacemaker and the heart. This procedure was necessary so that the physician could determine if the pacemaker programming was satisfactory.

Of course, this prior approach was time consuming and uncomfortable for the patient, especially if it had to be repeated several times for different operational parameters. In the present invention, the user is given the opportunity to enter a new set of parameters and to have the programmer simulate the operation of the pacemaker and the heart in accordance with these parameters. This may be accomplished as discussed above by asking the physician whether a simulation is desired or not. If a simulation is requested, then new parameters for the simulation are obtained from the user, via the keyboard 14, or down loaded from the patient's heart via the pacemaker. Of course, as well known in the art, the user does not enter all the necessary operational parameters necessary for the pacemaker. Rather, the user provides certain preselected parameters such as age and sex of the patient, physical condition, upper and lower pacing rates, and so on. The remainder of the parameters are calculated by the cardiac simulation device 22.

The new set of parameters are provided to the graphic elements generators. The graphic elements are then generated in the same manner as the actual parameters in steps S110–S114 as discussed above. (FIG. 2). A box 62 is provided on the screen 32 to indicated whether the represented graphic elements are based on the actual or simulated data.

After the graphic elements are displayed as shown in FIG. 3, in step S120 a check is performed to determine if actual or simulated graphic elements are displayed. If the parameters are actual then the microprocessor returns to a standby mode and waits for further instructions. If the data is simulated, then in step S122 the user is requested to indicate whether the newly selected parameters are acceptable. If the parameters are acceptable, then in step S124 the selected parameters are sent or downloaded to the implant 38 and the operation of the programmer 10 is complete. If the parameters are unacceptable, then in step S126 new parameters are selected and the microprocessor 10 proceeds to step S109 (FIG. 2).

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. A graphic display apparatus for displaying information on a screen related to the operation of a cardiac implant and associated cardiac functions, said apparatus comprising:

selection means for selecting an operational parameter;

simulating means for simulating the operation of said cardiac implant in response to said operational parameter based on the patient's own physiological responses to generate a simulation parameter;

first generating means for generating a first graphic image descriptive of a first cardiac parameter from said information;

second generating means for displaying a second graphic image descriptive of a dependency between said first and a second cardiac parameter; and indicia generating means for generating indicia interrelating said first and second images;

wherein said first and second cardiac parameters comprise one of an actual and said simulated parameters.

2. The apparatus of claim 1 further comprising display means for displaying said first and second images and said indicia on said screen.

3. the apparatus of claim 1 wherein said actual parameters comprise information derived from one of said patient and said cardiac device.

4. The apparatus of claim 1 further comprising simulation means for selecting a set of simulated parameters, said first and second parameters being selected from said set of simulated parameters.

5. The apparatus of claim 4 further comprising third generating means for generating a third image representative of said simulated parameters and selection means for selecting said first and second parameters from said image.

6. The apparatus of claim 5 wherein said selection means includes image moving means for moving said images in a superimposing relationship.

7. A graphic user interface for a cardiac implant, said implant being constructed and arranged for implantation in a patient, said interface comprising:

means for receiving data including information descriptive of an operation of said patient's heart and information descriptive of an operation of said implant;

means for simulating the operation of said cardiac implant in response to an operational parameter based on the patient's own physiological responses to generate a simulated parameter;

means for generating a first and second image corresponding to a first cardiac parameter and a second cardiac parameter characterized by said data;

means for generating an indicia descriptive of a relationship between said first and second cardiac parameter; and means for superimposing said indicia on said images;

wherein at least one of said first and second parameters comprises said simulated parameter.

8. The interface of claim 7 wherein said first parameter comprises a rate responsive parameter and said second parameter is an ECG obtained from said patient.

9. The interface of claim 7 wherein said first image corresponds to an ECG and said second image comprises a time-dependent graph of various cardiac events.

10. The interface of claim 7 further comprising simulating means for generating simulated parameters, one of said first and second parameters being selected from said simulated parameters.

11. The interface of claim 7 further comprising programming means for generating programming parameters for said implant based on said images.

12. The interface of claim 7 further comprising means for generating a graphic cardiac image related to said heart, means for generating selection points on said graphic cardiac means and means for pointing to one of said selection points.

13. The interface of claim 12 further comprising data display means for displaying selected data responsive to one of said selection points.

14. An apparatus for interrogating and configuring an implanted device, said implanted device being constructed and arranged to apply therapy to a biological organ such as the heart of a patient, said apparatus comprising:

a parameter selector for selecting an operational parameter for said implanted device;

a simulator for simulating an operation of said implanted device in response to said operational parameter based on the patient's own physiological responses, and generating a simulated parameter;

a display for displaying said simulated parameter.

15. The apparatus of claim 14 further comprising a transmitter for transmitting said operational parameter to said implanted device to configure said implanted device to an operational mode in accordance with said operational parameter.

16. The apparatus of claim 14 wherein said display displays a time-dependent image of said simulated parameter, said time dependent image being displayed in real time.

17. The apparatus of claim 14 further comprising an event sequence generator for generating a sequence of actual or simulated events for said implanted device based on said operational parameter, said sequence being displayed by said display.

18. The apparatus of claim 14 wherein said parameter selector is used to select a first and a second operational parameter, said simulator generating said simulated parameter corresponding to at least one of said first and second operational parameters, said apparatus further including a relationship generator for generating a time-independent relationship between said parameters, said display further displaying said relationship.

19. The apparatus of claim 14 wherein said implanted device includes a memory for holding a patient specific operational characteristic of said implanted device.

20. The apparatus of claim 19 further comprising a receiver for receiving said operational characteristic, said operational characteristic being displayed on said display.

* * * * *